US008060383B2

(12) United States Patent
Badinelli

(10) Patent No.: US 8,060,383 B2
(45) Date of Patent: *Nov. 15, 2011

(54) SYSTEMS AND METHODS FOR A CONSUMER TO DETERMINE FOOD/MEDICINE INTERACTIONS

(76) Inventor: Ellen Badinelli, West Nyack, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/886,216

(22) Filed: Sep. 20, 2010

(65) Prior Publication Data

US 2011/0054930 A1 Mar. 3, 2011

Related U.S. Application Data

(63) Continuation of application No. 12/020,306, filed on Jan. 25, 2008, now Pat. No. 7,805,319, which is a continuation of application No. 10/437,582, filed on May 14, 2003, now abandoned, and a continuation-in-part of application No. 10/272,596, filed on Oct. 16, 2002, now abandoned.

(60) Provisional application No. 60/380,736, filed on May 14, 2002, provisional application No. 60/329,927, filed on Oct. 17, 2001.

(51) Int. Cl.
*G06Q 10/00* (2006.01)
*G06Q 50/00* (2006.01)
*G06Q 40/00* (2006.01)
(52) U.S. Cl. ..................... 705/3; 705/2; 705/4
(58) Field of Classification Search .......... 705/2–4
See application file for complete search history.

(56) References Cited

U.S. PATENT DOCUMENTS

| | | | |
|---|---|---|---|
| 5,478,989 A | 12/1995 | Shepley | |
| 5,950,630 A * | 9/1999 | Portwood et al. | 128/897 |
| 5,991,730 A | 11/1999 | Lubin et al. | |
| 6,401,072 B1 * | 6/2002 | Haudenschild et al. | 705/3 |
| 6,539,101 B1 | 3/2003 | Black | |
| 6,542,902 B2 * | 4/2003 | Dulong et al. | 1/1 |
| 6,652,455 B1 * | 11/2003 | Kocher | 600/300 |
| 6,952,695 B1 * | 10/2005 | Trinks et al. | 1/1 |
| 6,980,999 B1 * | 12/2005 | Grana | 707/803 |
| 7,076,438 B1 * | 7/2006 | Tobelmann et al. | 705/7.32 |
| 7,343,330 B1 * | 3/2008 | Boesjes et al. | 705/28 |
| 7,613,634 B2 * | 11/2009 | Siegel et al. | 705/26.62 |
| 7,805,319 B2 | 9/2010 | Badinelli | |

(Continued)

FOREIGN PATENT DOCUMENTS

CA 2306674 10/2001

(Continued)

OTHER PUBLICATIONS

Business Editors and Health/Medical Writers, New Online Tool from MedicineNet gives Consumers Free Information to Avoid Harmful Drug/Drug & Drug/Food Interactions, Business Wire, Nov. 29, 2001, p. 1.*

(Continued)

*Primary Examiner* — Jason Dunham
*Assistant Examiner* — Amber Altschul
(74) *Attorney, Agent, or Firm* — Greenberg Traurig, LLP

(57) ABSTRACT

One embodiment of the present invention relates to systems and methods for detecting harmful and/or hazardous ingredients that may cause an allergic reaction, interfere with the effectiveness of a prescription drug, exacerbate symptoms associated with a chronic illness, and/or cause another undesired reaction.

5 Claims, 9 Drawing Sheets

U.S. PATENT DOCUMENTS

| | | |
|---|---|---|
| 2001/0056359 A1 | 12/2001 | Abreu |
| 2002/0032582 A1* | 3/2002 | Feeney et al. ............ 705/2 |
| 2004/0006494 A1 | 1/2004 | Badinelli |
| 2004/0078218 A1 | 4/2004 | Badinelli |
| 2004/0256454 A1* | 12/2004 | Kocher ............ 235/382 |
| 2008/0263011 A1 | 10/2008 | Badinelli |

FOREIGN PATENT DOCUMENTS

| | | |
|---|---|---|
| EP | 1117055 | 7/2001 |
| GB | 2313940 | 12/1997 |
| GB | 2325550 | 11/1998 |
| JP | 09050426 | 2/1997 |
| JP | 2002024399 | 1/2002 |
| JP | 2002041667 | 2/2002 |
| WO | 98/38589 | 9/1998 |
| WO | 01/13317 | 2/2001 |

OTHER PUBLICATIONS

European Search Report from EP 1 363 225 dated Sep. 14, 2004.

* cited by examiner

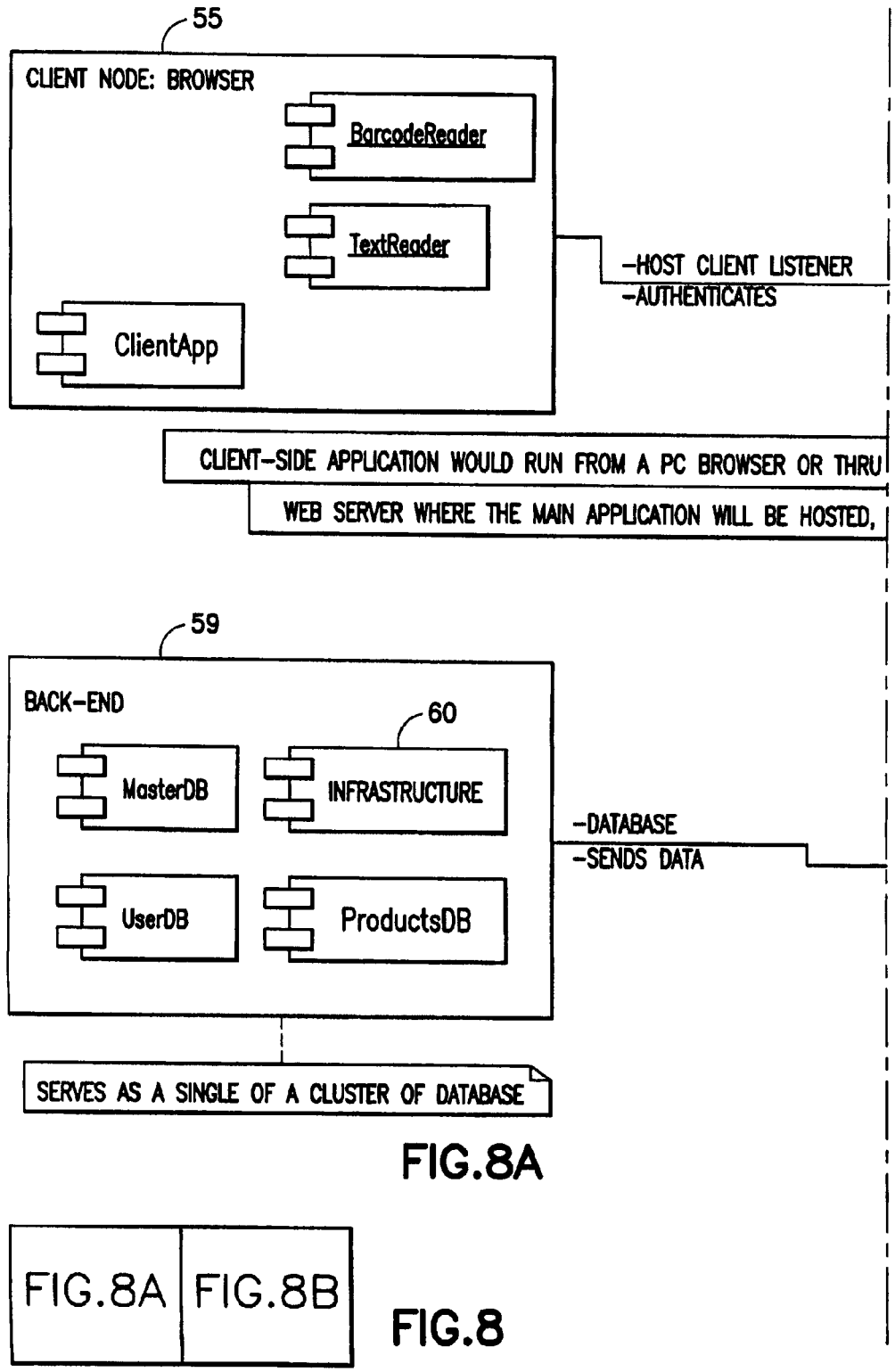

SYSTEMS AND METHODS FOR A CONSUMER TO DETERMINE FOOD/MEDICINE INTERACTIONS

RELATED APPLICATIONS

The present application is continuation of U.S. Appl. No. 12/020,306 now U.S. Pat. No. 7,805,319, filed Jan. 25, 2008, which is a continuation of U.S. Ser. No. 10/437,582, filed May 14, 2003 now abandoned, which is based on U.S. Ser. No. 60/380,736, filed May 14, 2002 and is also a continuation-in-part of U.S. Ser. No. 10/272,596, filed Oct. 16, 2002 now abandoned, which is based on U.S. Ser. No. 60/329,927, filed Oct. 17, 2001, each of which is incorporated herein by reference in its entirety for all purposes.

FIELD OF THE INVENTION

One embodiment of the present invention relates to systems and methods for detecting harmful and/or hazardous ingredients that may cause an allergic reaction, interfere with the effectiveness of a prescription drug, exacerbate symptoms associated with a chronic illness, and/or cause another undesired reaction (for the purposes of this application, such a harmful and/or hazardous ingredient that may cause an allergic reaction, interfere with the effectiveness of a prescription drug, exacerbate symptoms associated with a chronic illness, and/or cause another undesired reaction may be referred to as an "unwanted ingredient").

Another embodiment of the present invention provides for the detection of such unwanted ingredients (e.g., as mentioned in the nutritional and/or composition labels for food, beverage and/or drug products) on a real-time automated basis in places where these commodities are sold, prepared and/or served (e.g., including, but not limited to, supermarkets, restaurants and/or related businesses (e.g., in the hospitality industry, camps, schools, manufacturers, health care and/or home care facilities)).

For the purposes of this application, the term "store manager", "administrator", and "actor" may be used essentially interchangeably within the business environments described above.

Further, for the purposes of this application, the term "real-time" is intended to refer to a process that happens at once or essentially instantaneously (as opposed to a process that is completed in parts or over an extended time period (wherein such extended time period comprises, for example, a time period of a few hours or overnight)).

BACKGROUND OF THE INVENTION

The American Academy of Allergy, Asthma and Immunology estimates that 2% of adults and 8% of children in the United States are afflicted with food allergies (an estimated total of 7 million Americans according to the Food Allergy and Anaphylaxis Network). The allergic family represents an estimated $25 billion of grocery spending per year.

Allergies are believed the leading cause of chronic disease in United States, costing the healthcare system about $18 billion dollars annually. It is estimated that 150-200 people die each year from food allergies. Food allergy is believed the leading cause of anaphylaxis outside a hospital setting accounting for approximately 30,000 emergency room visits and 2,000 hospitalizations. The Epinephrine injection is the most effective method of treating anaphylaxis; however in a 1999 study conducted by Mt. Sinai Medical Center, only 32% of 101 parents administered it correctly, and only 21% of physicians administered it correctly.

In a 1999 study by the Mt. Sinai Medical Center, 91 sets of parents were asked to identify products whose ingredients their children must avoid. The most restricted food groups, peanut products and milk products, yielded correct answers in only 54% and 7%, respectively.

Indeed, reading labels to ensure they do not contain any harmful or unwanted product may be a complex and time consuming process. There are more than 30 essentially synonymous terms for milk alone.

Moreover, some labels may identify an ingredient, such as mayonnaise, without specifying its sub-ingredient such as "egg" (while individuals with egg allergies must avoid those products as well).

The NCPI (National Council on Patient Information) estimates that 95% of individuals over 65 (i.e., 32 million Americans) receive daily prescriptions (an average of 2.4 prescriptions per person). This group accounts for 13.4% of the population but accounts for 42% of total outpatient prescription spending.

In a study reported in the Jun. 12, 2002 issue of Annals of Emergency Medicine relating to elderly patients admitted to an urban hospital ER, the average number of prescriptions medications per patient was six. However, only 42% of these patients could correctly identify their medications. Additionally only 15% could identify their medication's indications.

Further, in a long-awaited national study conducted by the University of Wisconsin-Madison, (findings released by the FDA Jun. 18, 2002) regarding the distribution and "usefulness" of the medicine leaflets, one of every three leaflets received a low score, "1" or "2", out of 5, for print size, print quality, line spacing and ease of reading.

Additionally, merely the process of reading food labels may pose great difficulty for the following individuals:

The visually impaired who may strain to read the fine print of nutritional labels.

Individuals whose main language is not English.

Individuals who suffer from learning disabilities, dyslexia, or struggle with literacy.

Any individual who falls under the American with Disabilities Act, ADA, whose manual dexterity compromises their ability to read labels, e.g. those suffering from Parkinson Disease, Cerebral Palsy, Muscular Dystrophy, etc.

SUMMARY OF THE INVENTION

The present invention may be used, for example, by any individual whose dietary regimen has specific restrictions and/or requirements for a variety of health and/or nutritional reasons.

Further, the present invention may be used by anyone who wishes to receive information in an automated format (and thereby reduce the human error associated with correctly reading, deciphering and interpreting nutritional terminology).

Under one embodiment of the present invention customers are able to scan their products and their barcode subscriber card in order to receive real-time information related to the compatibility between the product they scanned and their profile (the present invention may employ mobile wireless scanners, point of sale (POS) terminals, and/or stationary self-service terminals). The profile may contain information regarding a customer's allergies, prescriptions, chronic illness and conditions, and/or specific dietary requirements. The system may translate various terminologies used in nutritional and/or ingredients labels, compare the composition information with the customer's profile, and alert the customer to the presence of harmful ingredients and/or a prescribed food substance.

The present invention may generate an alarm for any substance and/or ingredient contained in a product (including Over The Counter substances and/or products) that will cause an undesired, harmful and/or allergic reaction, interfere with the effectiveness of a prescription drug, and/or exacerbate symptoms associated with a chronic illness. Of note, for the purposes of the present application the term "Over The Counter" is intended to refer to any medicines, vitamins, supplements, etc. which are available without a prescription.

As an example illustration of use of an embodiment of the present invention, a parent shopping in a supermarket will be able to check that products he or she is purchasing are compatible with the identified allergy of his son (for example tree-nuts), or does not contain substances he or she wishes to avoid (for example: The Feingold Diet recommends removal of Yellow dye #5 in the diet of a child diagnosed with Attention Deficit Hyperactivity Disorder).

As another example illustration of use of an embodiment of the present invention, an elderly person will easily check the compatibility his or her prescriptions and any product purchased Over The Counter and/or in the grocery aisles.

Illustrates the system architecture and provides a physical view of tiers involved in the overall system according to an embodiment of the present invention.

Figure 2:
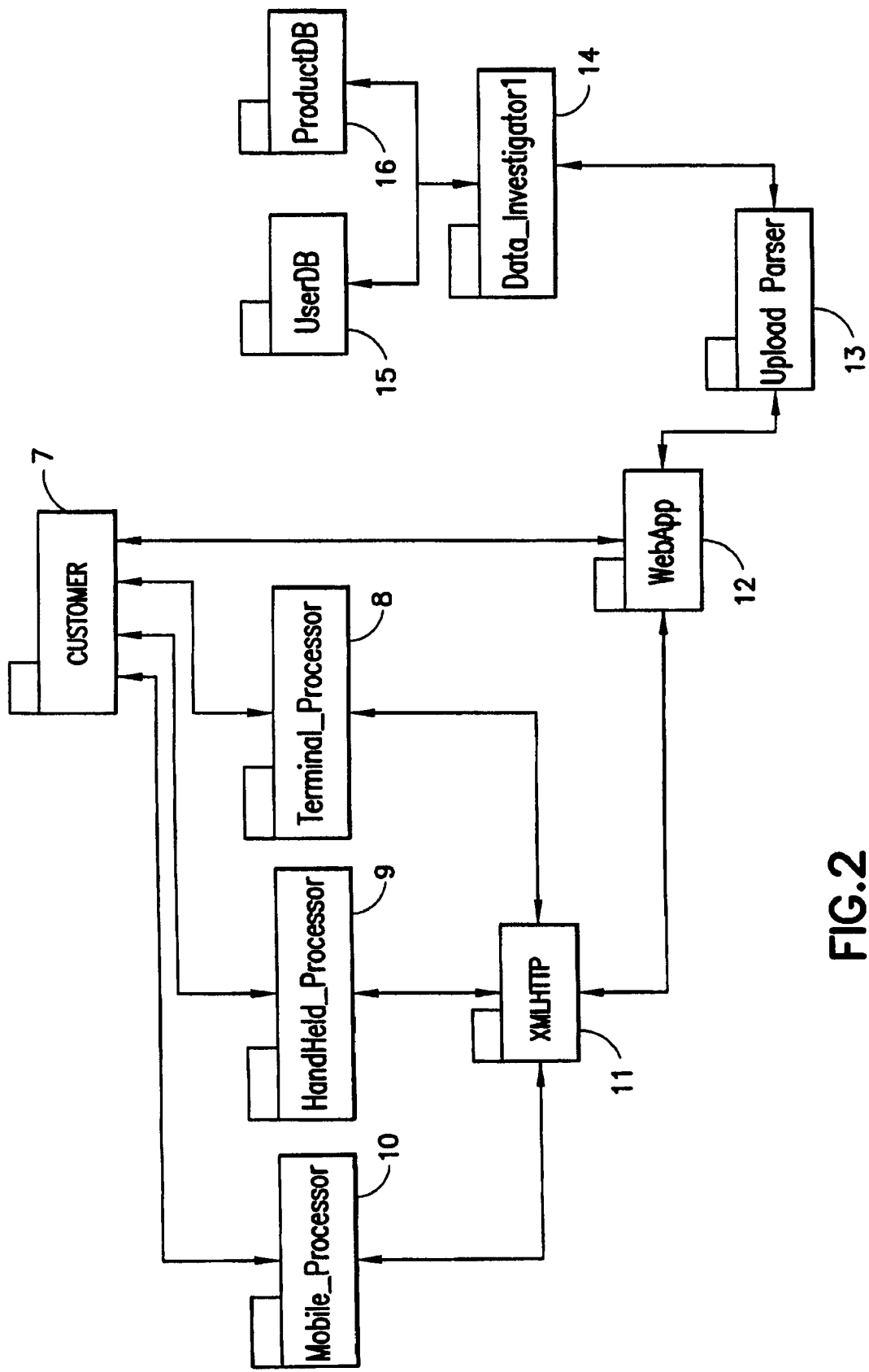

FIG. 2: Package Diagram

Illustrates an embodiment of the present invention blown-up into logical packages that would function in tandem to work as a full-fledged system.

Figure 3:
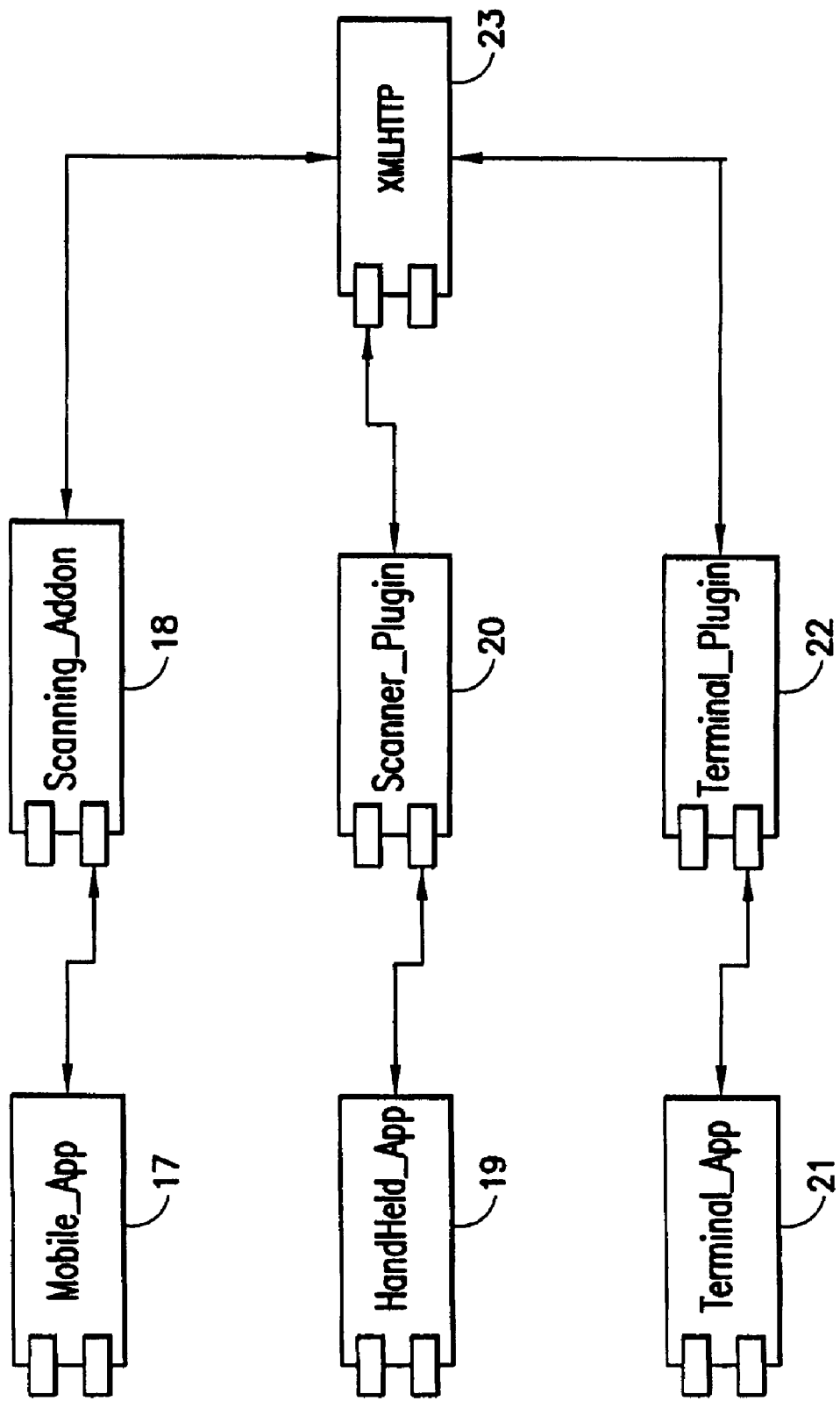

FIG. 3: Client-side Class Diagram

Illustrates an embodiment of the present invention showing a schematic of the client-side interface and various objects that would participate at the user end.

Figure 4:
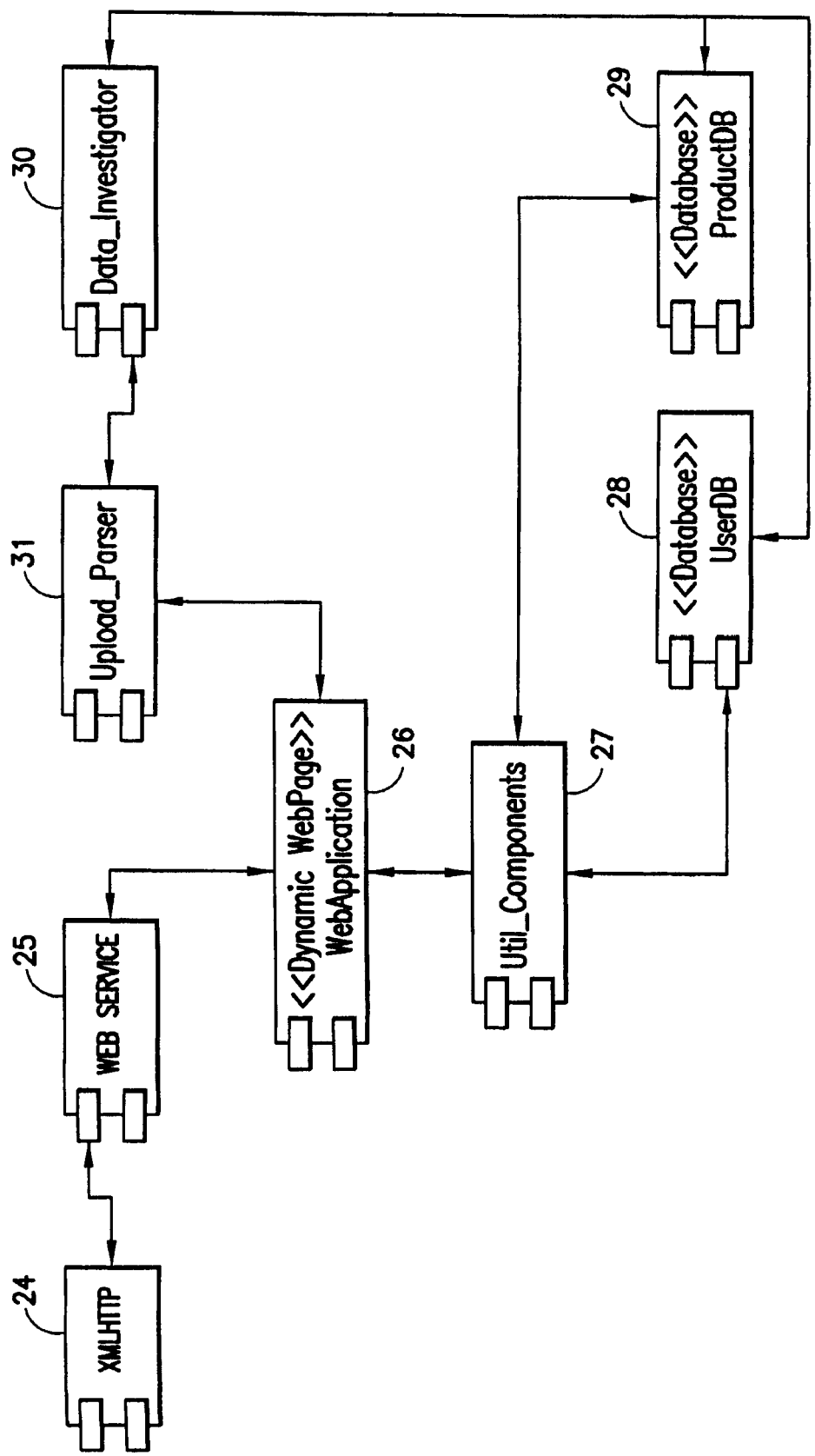

FIG. 4: Server-side Class Diagram

Illustrates an embodiment of the present invention showing a schematic of the server-side interface and various objects that would participate at the server end (thereby correlating an n-tier architecture followed by the system).

Figure 5:
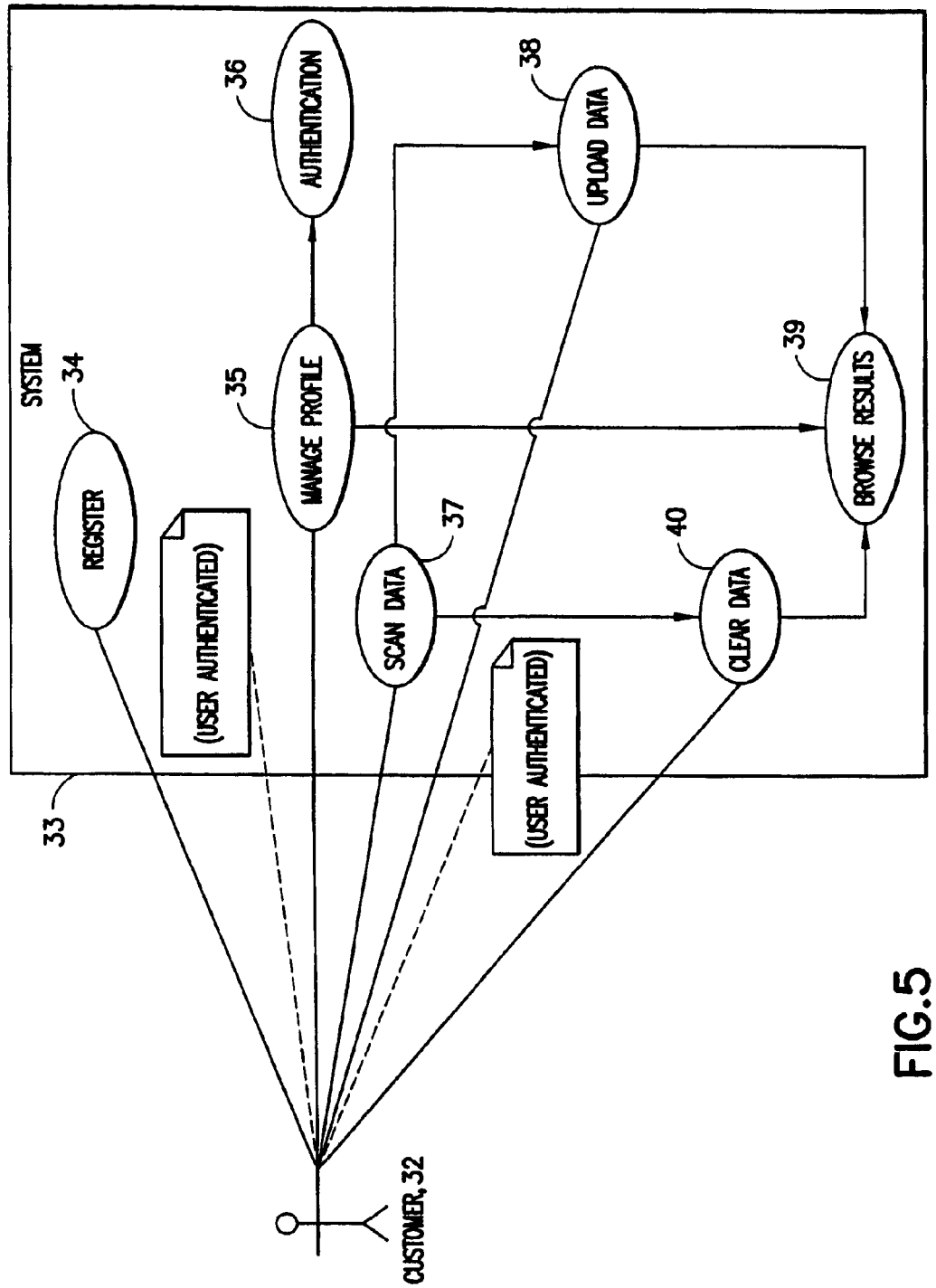

FIG. 5: High Level Use Case Diagram for Customer

Illustrates an embodiment of the present invention showing possible scenarios under which the customer would interact with the system.

Figure 6:
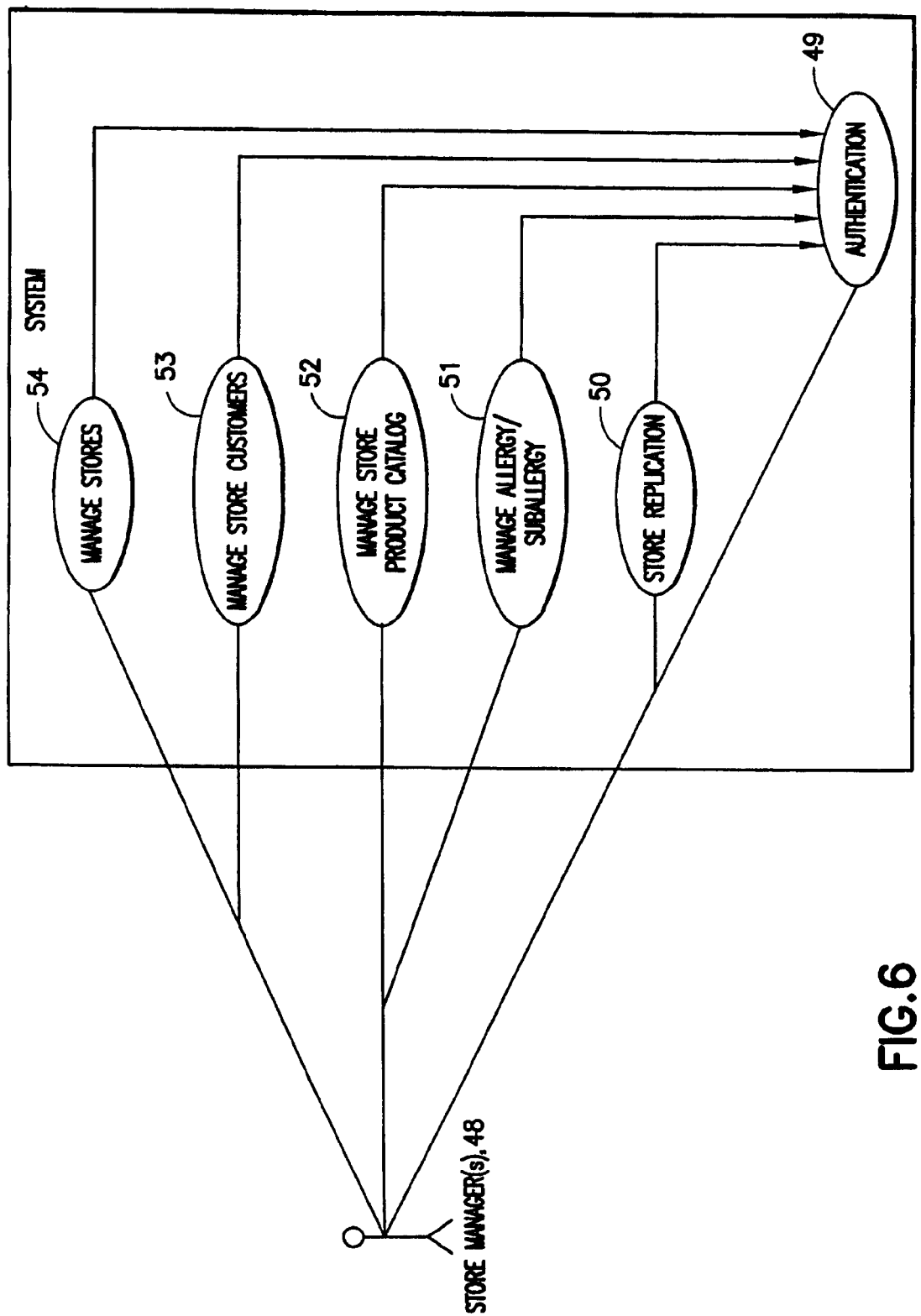

FIG. 6: High Level Use Case Diagram for Store Manager (s)

Illustrates an embodiment of the present invention showing possible scenarios under which the store manager(s) would interact with the system.

Figure 7:
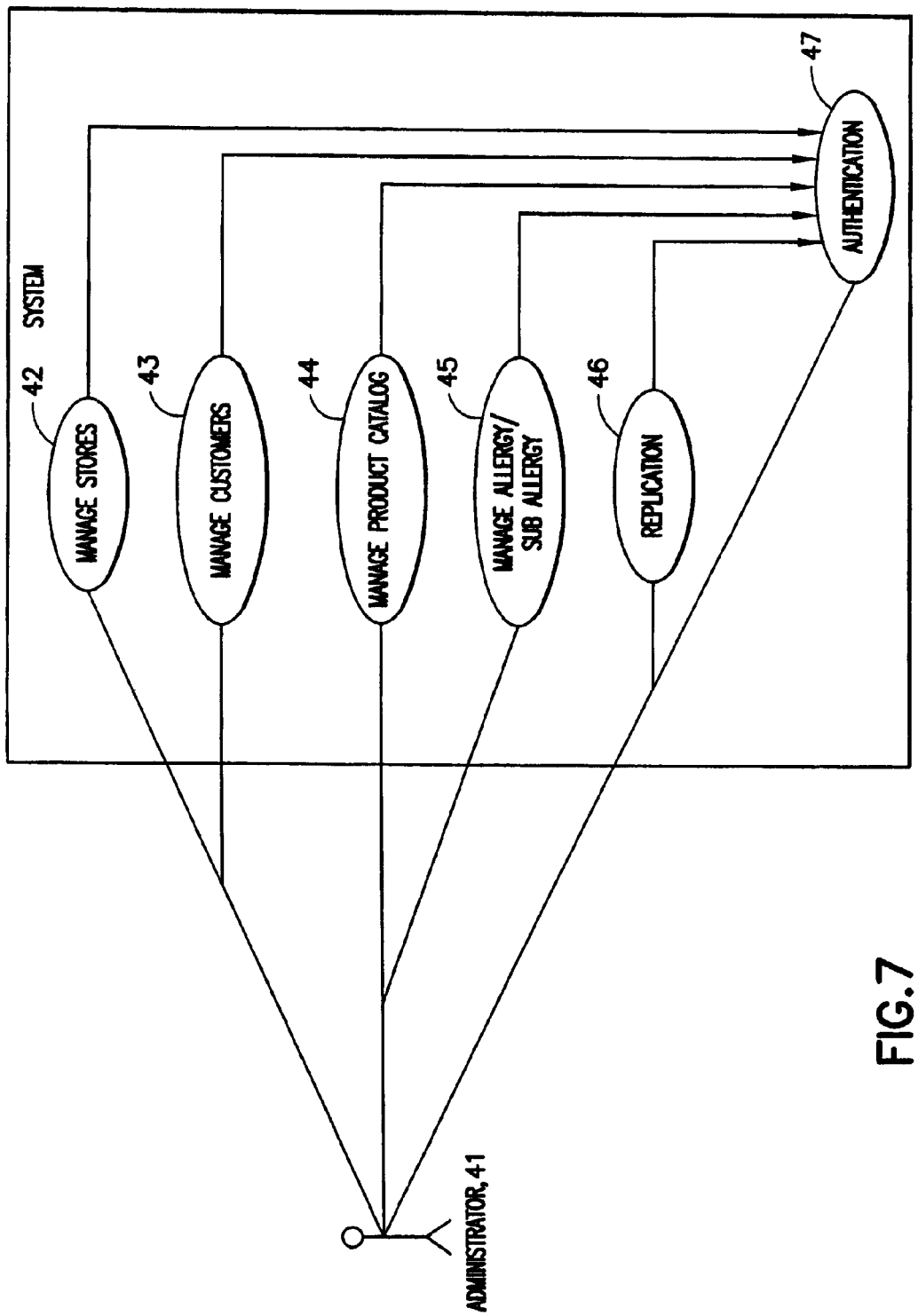

FIG. 7: High Level Use Case Diagram for Administrator

Illustrates an embodiment of the present invention showing possible scenarios under which the administrator would interact with the system.

Figure 8B:
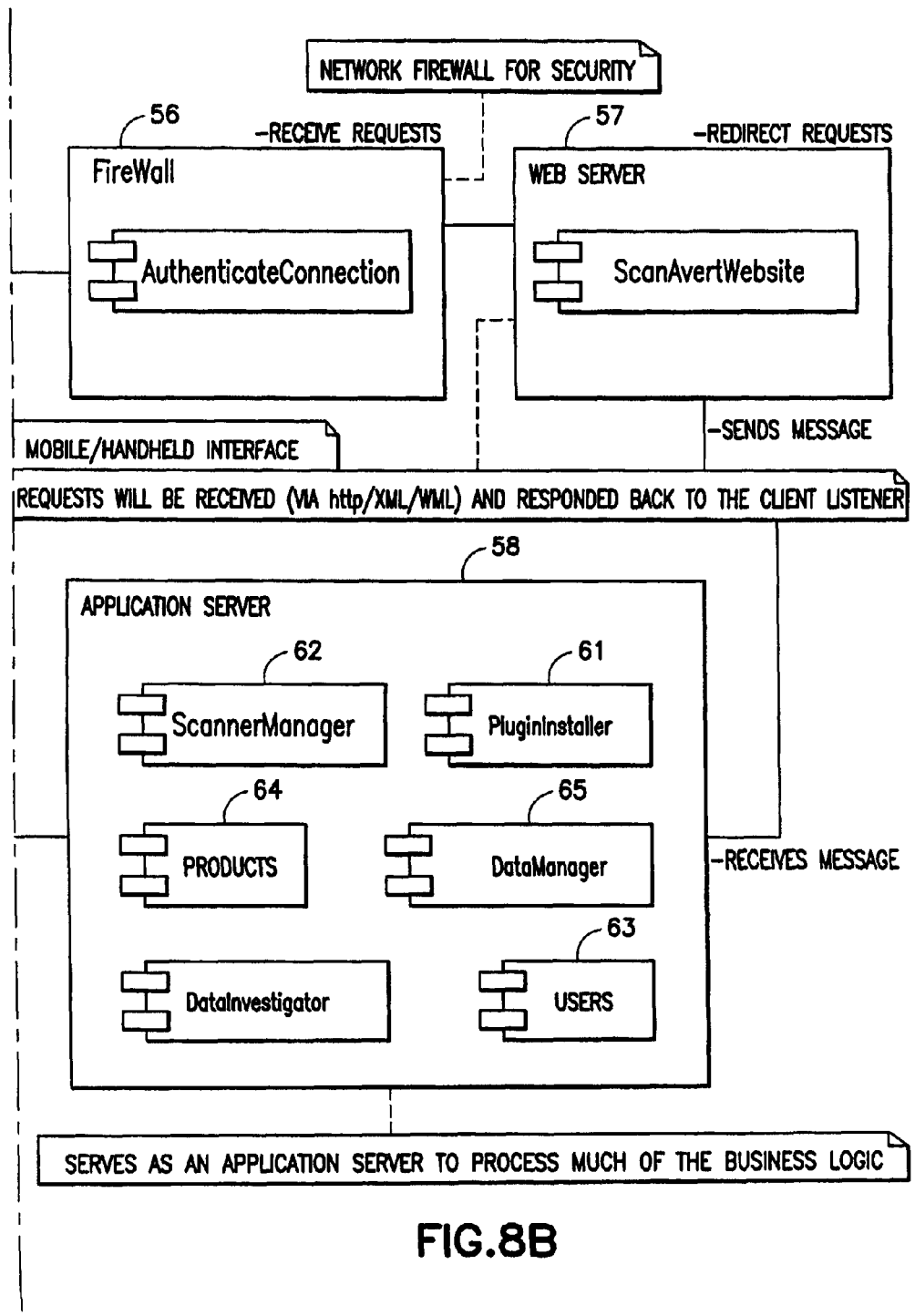

FIG. 8: Deployment Diagram

Illustrates an embodiment of the present invention showing the implementation level architecture providing an overview of how the system would be deployed.

Among those benefits and improvements that have been disclosed, other objects and advantages of this invention will become apparent from the following description taken in conjunction with the accompanying figures. The figures constitute a part of this specification and include illustrative embodiments of the present invention and illustrate various objects and features thereof.

DETAILED DESCRIPTION OF THE INVENTION

Detailed embodiments of the present invention are disclosed herein; however, it is to be understood that the disclosed embodiments are merely illustrative of the invention that may be embodied in various forms. In addition, each of the examples given in connection with the various embodiments of the invention are intended to be illustrative, and not restrictive. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

Figure 1:
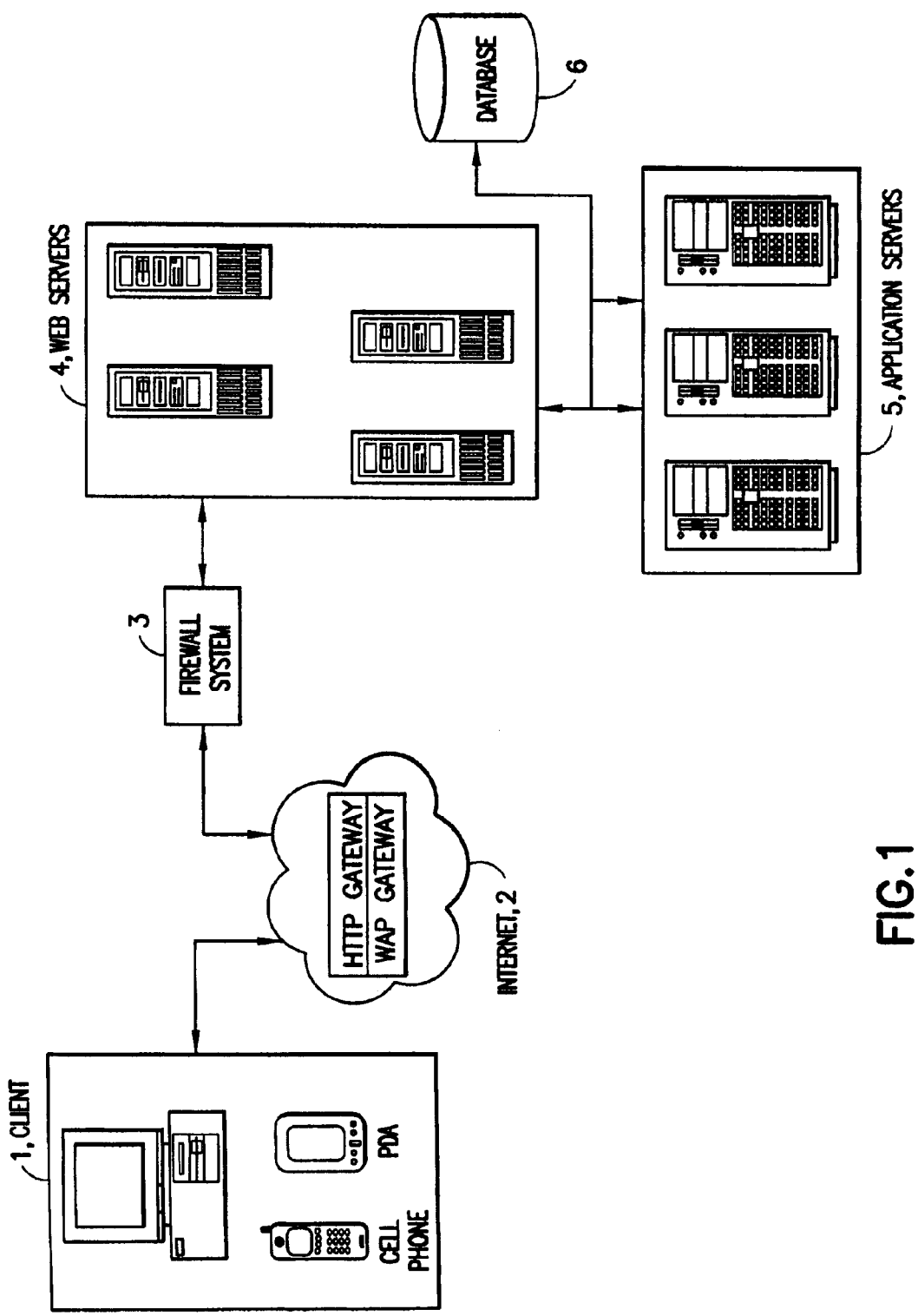
FIG. 1: System Architecture (Physical View)

Referring now to FIG. 1, one embodiment of the present invention is shown. Under this embodiment of the present invention the system has been conceived to work in an n-tier architecture, where the customers would be provided with multiple ways to interact with the system. More particularly, FIG. 1 shows that the Client-end 1 would allow various devices like computers, PDA, mobile phones, static terminals installed in the store location and other handheld devices to scan item barcodes and/or nutrition labels and compare that information with the customer's nutrition profile (the term customer profile may herein after be used synonymously with nutrition profile). In one example (which example is intended to be illustrative and not restrictive) the client interface maintains a connection to the Internet via the customer's Internet Service Provider (ISP) and/or by using the connection available at the store location. FIG. 1 illustrates the system architecture and provides a physical view of the tiers involved in the overall system according to this embodiment. The Client-end 1 may include devices as well as the client application that the customers would use to access the system. The client application could be browser-based and may be accessed from desktops or kiosks, or small devices such as handhelds, mobile phones, or add-ons, that would be embedded into static terminals or small devices such as handhelds or mobile phones. The Client-end 1 may interact with the system via an Internet connection 2. WAP enabled devices such as mobile phones and PDAs may interact with the system through a WAP gateway provided by ISPs. All requests for service may be authenticated for security by a Firewall system 3.

Once the requests have been authenticated by the Firewall system 3, they are received by the web application system that, in one example (which example is intended to be illustrative and not restrictive), could be a cluster of web servers 4 serving the application in collaboration with application servers 5 and the backend database system 6 to perform all necessary processing. Once the requests have been processed, the web application may then create a static document that would contain the response to the request after the processing was completed. This response may then be redirected to the client interface that invoked the request through their respective devices. Typical requests made by the Client-end 1 would be to register for the system, thereby enabling them to use scanning capable devices/equipment to get product information, upload device data (handheld scanners, static terminals, mobile phones and handheld devices with inbuilt scanners), upload product information, and compare the product information against their profile.

In another embodiment the present invention provides a method relating to the input, output and analysis of product information against a customer profile to provide data about a potentially harmful substance and/or a substance that the customer chooses to avoid for health and/or other reasons. In this regard, food allergies and interference with prescription drugs are common examples of the necessity for harmful reaction detection to prevent consumption of ingredients not suited and/or intended for a specific individual. Disease or illness management, e.g., Diabetes, Celiac Disease, or religious observance e.g., Kosher, are other compelling reasons for such consumption avoidance.

In one embodiment the present invention may use scanning technologies to enable users to use text scanners and/or barcode scanners to get information about a potentially harmful substance and/or a substance that the customer chooses to avoid for health and/or other reasons. The data may be entered by individuals or others (e.g., a pharmacist) with input devices capable of OCR-based scanning, by scanning a "Customer Care Card" followed by scanning the barcodes and/or ingredient labels of the items they are interested in. This information may then uploaded to a web application (e.g., of the type referred to in FIG. 1) and a translation of data may take place. For example (which example is intended to be illustrative and not restrictive): First the Customer barcode is interpreted followed by item barcodes. The customer barcode is then checked against the database to be associated with a customer profile. As stores might be using their own user database, a replication feature may be provided to store managers and administrators to replicate their database with the central database of the system. The customer profile is then temporarily stored in the process space of the web-application. The item barcodes are then checked against the database. The item information (e.g., Name, Composition and Ingredients) are stored in the process space of the application. This is compared against the customer profile. The results are stored in a static document and then sent back to the client application that invoked the request. In on example (which example is intended to be illustrative and not restrictive) the upload request can be made in two modes: persistent data detection and manual upload. In persistent data detection mode, the device constantly waits for data. This may apply to small devices such as a handheld or mobile phones, where large amount of data cannot be stored. As soon as data is received by the device, it may be "pushed" via the Internet to the web application system for interpretation. This would mean that the user would view information about the items one by one. In manual upload mode, the user invokes the upload of data from the device to the web application system, thereby allowing them to make multiple scans and "push" a set of item barcodes to the system.

In this regard, there is another aspect considered by this embodiment of the present invention in connection with the persistent data scanning mode. Since the "push" takes place as soon as the scan occurs, the user profile may have to be available beforehand. This could imply that the client application to be used by handheld or mobile devices might ask the user to get authenticated before they start scanning items or allow a small plug-in to be installed in these devices that would store the customer profile before hand.

With reference now to the embodiment shown in FIG. 2, an illustration depicting components grouped together based on their nature and the tier they are fitted in is shown. The Customer (Client) Package 7 represents the client application that would be used to access the service. The client application could be, for example, browser-based static web pages served to computer terminals, kiosks, web enabled PDAs and/or mobile phones by the server-based Web Application System or could be a software plug-in embedded into the device itself thereby preventing the user having to authenticate themselves each time they want to use the system. Mobile Processor, Handheld (Scanner) processor and terminal process 10, 9, and 8 respectively represent the processing that would be initiated by the client-application and serves to illustrate a scenario where multiple interfaces could be used by the customer to access the application.

In one example (which example is intended to be illustrative and not restrictive) all operations requested by the client-end processor could be sent via simple http using browser protocols and/or an XML package 11 on the client-end that would provide a more structured and platform-independent way to address all the requests from these different devices from a common platform. The XML package 11 represents the client-side process that would actually send data in and out of the client-application and therefore represents the purpose and not a necessity that using XML would be the only way. This package could be replaced by any package that would provide features fulfilling the purpose described in this section.

In one example (which example is intended to be illustrative and not restrictive) all requests coming to the server may be redirected to the web application 12, which then interprets the requests and processes them using the components installed on the application server. A typical upload request would be redirected for parsing to the Upload Parser package 13 that includes a set of components instantiated depending on the device information. For example (which example is intended to be illustrative and not restrictive): After the parser package finishes filtering the barcodes, the first barcode is assumed to be a user barcode and is run against the database UserDB 15 to extract the customer profile. If matches are not found against the UserDB 15, the upload parser may send a message to the web application 12 to indicate an "abort". If the customer profile is found then the rest of the barcodes are compared against the ProductDB 16 for item information. Thus, we get two set of data, namely customer profile including the allergies, sub allergies, and/or ingredients that the customer has to refrain from consuming and a set of ingredients and/or composition information for each item uploaded by this customer. This information is then taken by the data investigator package 14. The data investigator package 14 then runs a comparison between the two data explained earlier in this section and creates a result sheet including any essential alerts against the items uploaded and extensive information for the cause of this alert. The result sheet may be saved as a static document and sent back to the client-application via the web application.

Referring now to FIG. 3 and FIG. 4, these show additional illustration of classes (components) by separating the client-side processes and the server-side processes.

More particularly, FIG. 3 represents the client-side class diagram for an embodiment of the present invention. If we further break down the client-side processes, the client-side application would be broadly divided though not limited to three categories: Mobile_App 17 representing a client-side application that could be browser-based or stand-alone and used by PDAs, mobile phones and other small interactive devices with computing features and an inbuilt monitor and scanner, HandHeld_App 19 representing a browser-based application for users equipped with handheld personal barcode scanners that could be connected to a computer and Terminal_App 21 representing a client-side application installed on static terminals that could be used by customers at store locations. Scanner_Addon 18, Scanner_Plugin 20 and Terminal_Plugin 22 modularizes the process specific to the retrieval of data from the scanning device and converting into an intelligible piece of information that could be sent, for example, via XMLHTTP 23 to the web-application system.

Further, FIG. 4 represents the server-side class diagram for an embodiment of the present invention. After getting validated by the firewall system 3, a server-side component receives data sent by the client-side XMLHTTP 23 into a server-side XMLHTTP 24. The Web Service 25 represents the complete server-side system that includes the cluster of web servers serving the web application 26, the application server hosting components such as the Upload_Parser 31, Data$_{13}$Investigator 30 and util_Components 27 and the back-end database server hosting UserDB 28 and Product_Db 29. In one example (which example is intended to be illustrative and not restrictive), WAP requests will be converted into an http request by the web service before going through the common web application system. The Upload_Parser 31 could make use of the UserDB 28 and ProductDB 29 (e.g., by components associated with the Util_Components 27). The WebApplication 26 could also make use of the UserDB 28 and ProductDB 29 (e.g., by components associated with the Util_Components 27). A typical upload request would be redirected for parsing by the Upload Parser package 31 that includes a set of components instantiated depending on the device information. For example (which example is intended to be illustrative and not restrictive): After the parser package finishes filtering the barcodes, the first barcode is assumed to be a user barcode and is run against the database UserDB 28 to extract the customer profile. If matches are not found against the UserDB 28, the upload parser sends a message to the web application 26 to indicate an "abort". If the customer profile is found then the rest of the barcodes are compared against the ProductDB 29 for item information. Thus, we get two set of data, namely customer profile including the allergies, sub allergies, and/or ingredients that the customer has to refrain from consuming and a set of ingredients and/or composition information for each item uploaded by this customer. This information is then taken by the data investigator package 30. The data investigator package 30 then runs a comparison between the two data explained earlier in this section and creates a result sheet comprised of any essential alerts against the items uploaded and extensive information for the cause of this alert. The result sheet is saved as a static document and sent back to the client-application via the web application.

Referring now to embodiments shown in FIG. 5, FIG. 6 and FIG. 7, it is seen that these Figs. illustrate schema for various broad use cases depicting scenarios in which the actors (e.g., Customers, Store Manager(s) and Administrator) would interact with the system. Of note, the term "actor" is an abstraction for entities outside a system, subsystem or class that interact (e.g., directly) with the system. Further, a "use case" is a specification of sequences of actions, including variant sequences and error sequences, that a system, subsystem, or class can perform by interacting with actors.

More particularly, FIG. 5 illustrates a high level use case diagram for customers interacting with the system. Of note, in this embodiment customer 32 represents the end user who would be actually performing the scanning on items and/or uploading this information to the web application system 26. As seen in this FIG. 5:

A customer 32 could register to the web application system. This would create a barcode against the customer and also generate a customer care card. The customer 32 would then be able to download plug-in 18, 20 and use the system for scanning items and getting it validated.

A customer 32 could manage his customer profile subject to authentication using the web application system.

A customer 32 would scan item barcodes across stores or any recognized outlet where food and drugs are sold. The customer would also be able to use text scanners to scan nutrition and ingredient labels for products and validate it against his profile (e.g., via the plug-in 18 and 19).

A customer 32 would be able to Upload scanned data by an interface in a persistent data collection mode or manually.

A customer 32 would be able to clear scanner data (especially, but not limited to, personal barcode scanners).

A customer 32 would be able to access the web application system 26 for future reference if need be.

Further, FIG. 6 illustrates a high level use case diagram for store manager(s) interacting with the system. As seen in this FIG. 6:

Store manager(s) 48 would be able to manage their stores, outlets and sale location 54 via the system. In one example (which example is intended to be illustrative and not restrictive), this would only comprise managing data related to their specific stores that are subject to change and would be essential to be modified in the system as well.

Store manager(s) 48 would be able to manage store customers 53 data using their premises or services via the system.

Store manager(s) 48 would able to manage store product catalogs 52 limited to their store locations, outlets and sales location via the system. In one example (which example is intended to be illustrative and not restrictive) this would be subjected only to data maintained specifically by/for the store or outlet.

Store manager(s) 48 would be able to manage allergy, sub allergy and other hazardous constituents 51 recognized and validated by the system. In one example (which example is intended to be illustrative and not restrictive), this would be subjected only to data maintained specifically by/for the store or outlet.

Store manager(s) 48 would be able to replicate 50 the central database server components UserDB 28 and ProductDB 29 to be in sync with data available in external user and product databases hosted by the stores, outlets and sales locations. In one example (which example is intended to be illustrative and not restrictive), this would be subjected only to data maintained specifically by/for the store or outlet.

Store manager(s) 48 would be strictly subjected to Authentication 49 to perform any of the mentioned activities.

Further still, FIG. 7 illustrates a high level use case diagram for an administrator interacting with the system. As seen in this FIG. 7:

An administrator 41 would be able to manage all stores, outlets and sales location 42 via the system.

An administrator 41 would be able to manage all customers 43 via the system.

An administrator 41 would able to manage product catalogs 44 on behalf of stores, outlets and sales locations where the consumables will be sold.

An administrator 41 would be able to manage Allergy, sub allergy and other hazardous constituents 45 recognized and validated by the system.

An administrator 41 would be able to replicate the central database server components UserDB 28 and ProductDB 29 to be in sync with data available in external user and product databases hosted by the stores, outlets and sales locations.

An administrator 41 would be strictly subjected to Authentication 47 to perform any of the administration activities.

Referring now to FIG. 8, implementation level architecture providing an overview of how a system according to an embodiment of the present invention would be deployed is illustrated. More particularly:

FIG. 8 embodies the various tiers that would comprise the system. The various nodes represent physical deployment of various components at various levels in the system.

The Client-node 55 may comprise two essential parts. The core scanning and upload feature may be provided by the textreader component and barcodereader component described earlier in this document as plug-in 18, 20 and 22. The second part in this node may be the client-application that would use plug-in 18, and 22 to interface with the system. The client-node may be accessible and configured to be used by multiple computer devices such as computer with a browser, WAP enabled phones and handhelds or static terminals installed onsite where the consumables will be sold.

The client-node 55 may present a different interface for Store Manager(s) and Administrator to perform activities illustrated in FIG. 6 and FIG. 7.

The firewall node 56 represents the set of security features provided at the server end of the system. This could be a set of hardware and/or software that may be, for example, manufactured, developed and/or supported by a recognized third party.

The web server node 57 represents the location where the web application 26 would be hosted. This may involve one or more than one web server working as a cluster. All static and dynamic webpages may be served from this node.

The application server node 58 represents the location where all server-side components would be hosted and utilized by the web server node 57.

Additional components such as plug-in installer 61 to provide embedded plug-in 18, 20 and 22 to be installed or served to the client-node may reside in the application server node 58.

Additional Components such as ScannerManager 62 may reside in the application server node 58. The ScannerManager 62 may track all scanners and maintain information regarding the use of the scanners.

Additional Components such as Users 63 may reside in the application server node 58. The Users 63 component may group all processes essential or invoked by/for users.

Additional Components such as Products 64 may reside in the application server node 58. The Products 64 component may group all processes essential or invoked for products.

Components such as DataManager 65 may reside in the application server node 58. The DataManager 65 component may group all processes essential or invoked for data replication as illustrated, for example, in FIG. 6 and FIG. 7.

The Back-End node may act as the central repository for UserDB 28 and ProductsDb 29. In addition to this, a MasterDB 66 may serve if desired to store information about the system in general.

The Back-end node 59 may also include the infrastructure 60 that has to be in place to allow fast and reliable information to the components hosted by the application server node 58 and the web server node 57.

An audible and/or visible alert may be sent to the user whenever an incompatibility is encountered. This could be detected and sent from the web server node 57 to the client node 55.

In another embodiment, by translating synonyms relating to the same ingredient, the present invention may allow an immediate and reliable detection of all ingredients related to one specific allergy.

In another embodiment, the present invention automatically performs the function of alerting consumers to harmful sub-ingredients that may not be specified clearly in the nutritional label.

In another embodiment, users/beneficiaries of the present invention may be: the allergy afflicted; individuals receiving prescription drugs; children (e.g., those whose physicians, neurologists, and/or other medical specialists advocate removal of certain ingredients from their diet as it is perceived to interfere with learning, e.g. Feingold Diet recommends a gluten-free and a food colorings-free (Yellow #5 and Red #3) diet to improve the focus of children diagnosed Attention Deficit Disorder (ADD) and Attention Deficit Hyperactivity Disorder (ADHD)); women who want to decrease the possibility of having a child with food allergies who are instructed by their doctor to refrain from consuming certain ingredients during their pregnancy; religious-observant (e.g., Kosher or Hindu); vegetarian; individuals with ingredient sensitivity (e.g. lactose intolerance or other ingredient sensitivity); individuals managing an illness and/or disease (e.g., such as individuals with digestive disorders and/or with chronic conditions (e.g., ulcers) which are aggravated by specific ingredients; children (e.g., those who may be receiving prescription medication for perceived learning disabilities (e.g., Ritalin or Adder all) who must refrain from certain OTC medications and/or food/beverage ingredients that may inhibit or suppress the effectiveness of the prescription or its duration).

In another embodiment, the system and method for this invention is disclosed and declared to elaborate various actors, entities and other physical and logical units that collaborate and participate through multiple scenarios and mediums to detect harmful ingredients in food, OTC remedies and related consumables as specified by their nutritional and ingredients labels that may cause allergic reaction, health risks or any incompatibility between prescription drugs and normal food/ingredient consumption of an individual, on an automated, real-time system. The invention may use scanning based technologies (e.g., Barcode Scanning and/or Text Scanning) as well as non-scanning based technologies via an interactive communication channel that could be used from a centralized access medium or an offline setup that: (a) translates various terminologies used in nutritional and ingredients labels; (b) compares the composition information with the customer's profile; and (c) alerts the customer to the presence of harmful ingredients or prescribed (recommended) food substance.

In another embodiment (hereinafter referred to as embodiment "A"), a computer-based system is provided. This computer-based system of embodiment "A" may permit a customer to determine the compatibility of food/medicine interactions on an automated real time basis by detecting harmful/incompatible ingredients in food, drugs and/or related consumables as specified by their nutritional and/or ingredients labels that may cause an allergic reaction, health risks and/or any incompatibility with the normal food habits or prescribed drug intake of a specific individual comprising. The system of embodiment "A" may comprise: (a) any suitable scanning device, such as barcode or text scanner for reading barcode or text on the product's label capturing information by scanning the item(s); (b) uploading the scanned information to a centralized or distributed system working with a single central repository or distributed repositories of product related information; (c) mapping the information uploaded with the nutrition and ingredients data; (d) comparing this data with a Customer Profile (as described, for example, in embodiment "B" below) with ingredients or composition that may be incompatible and/or cause allergic reaction an/or health risk and therefore is to be avoided, or, conversely, is professionally recommended as a dietary requirement and therefore included; and (e) generating an alert, which alert that signals the presence of harmful ingredients or required dietary ingredients, audibly and/or with adjoining text.

In another embodiment (hereinafter referred to as embodiment "B"), a computer-based system for a customer to determine the compatibility of food/medicine interactions on an automated real time basis may use Customer-Profile information. Such Customer Profile information may be stored, and said information may include harmful food substances, allergic ingredients in food, drugs and related consumables incompatible and/or harmful to the customer and/or wherein determined thresholds of specific substances, according to the nutritional information, are exceeded-establishing an Avoidance Profile, and/or conversely, dietary requirements and nutritional valuations beneficial to the customer, establishing a Requirement Profile.

In another embodiment (hereinafter referred to as embodiment "C"), a computer-based system for a customer to determine the compatibility of food/medicine interactions on an automated real time basis as described in connection with embodiment "A", wherein the information scanned is embedding Customer Profile information of embodiment "B", may include: (a) a scanning device, such as a barcode or text scanner, providing output information indicative of the information scanned; and (b) an application process that takes the data as an input and compares it with the stored Customer-Profile.

In another embodiment (hereinafter referred to as embodiment "D"), a computer-based system for a customer to determine the compatibility of food/medicine interactions on an automated real time basis is provided. This computer-based system of embodiment "D" may comprise: (a) a text-based scanning device providing product information by scanning the nutrition and ingredients labels of item(s); (b) handling this data via an embedded application as described in connection with embodiment "C"; (c) comparing this data with the Customer Profile as described in embodiment "B" for possible ingredients or composition that may cause allergy, health risks and/or might be prescribed as a healthy and necessary food substance; and (d) generating an alert to the customer, in an audible and/or visual signal, as to the presence of harmful ingredients and/or prescribed food substance and/or required dietary ingredients.

In another embodiment (hereinafter referred to as embodiment "E"), a computer-based system for a customer to determine the compatibility of food/medicine interactions on an automated real time basis is provided, comprising: (a) an application embedded into existing independent systems (e.g., upon an intent of use by the system owner), which application is able to: (i) execute upon the occurrence of an event (e.g., Search request, Add to Cart, etc.); and (ii) capture product information related, but not limited to, nutritional composition and ingredients of item(s); (b) comparing this data with the Customer Profile as described in connection with embodiment "B" for possible ingredients or composition that may cause allergy and/or health risks and/or might be prescribed as a healthy and necessary food substance; and (c) alerting the customer to the presence of harmful ingredients and/or prescribed food substance by sending an audible and/or visual signal.

In another embodiment (hereinafter referred to as embodiment "F"), a computer-based system to be used for processes described in connection with embodiments "A", D", and/or "E" is provided, comprising: a centralized application that would facilitate users to create their own Customer Profiles through an interactive channel specifying information related, but not limited to, allergies, illnesses, prescriptions and dietary requirements.

In another embodiment (hereinafter referred to as embodiment "G"), a computer-based system to be used for processes described in connection with embodiments "A", D", and/or "E" is provided, comprising: applications that would facilitate users to access their own Customer Profiles through different types of interactive channels, such as by scanning or swiping a barcode subscriber card, entering a login manually, recognizing finger prints as well as iris identification, or whatever auto-ID developing or evolving technology becomes standard, practiced or customary.

While a number of embodiments of the present invention have been described, it is understood that these embodiments are illustrative only, and not restrictive, and that many modifications may become apparent to those of ordinary skill in the art.

What is claimed is:

1. A system for determining food or medicine interaction of a user, comprising:
   1) a memory having at least one region for storing computer executable program code; and
   2) a processor for executing the program code stored in the memory, wherein the program code comprises:
   a) code to populate, by a programmable device, a database, that correlates at least:
      i) a first product identifier corresponding to at least one ingredient of a first product; and
      ii) a second product identifier corresponding to at least one ingredient of a second product;
   b) code to create and maintain via the Internet utilizing a web-based mechanism, at least a first user profile, comprising user health information for a plurality of users;
   c) code to capture, in real-time, a first product identifier received by scanning a first product by at least one hand-held communication device, wherein the first product includes indicia associated with the first product identifier;
   d) code to transmit, in real-time, the first product identifier from the at least one hand-held communication device to the database;
   e) code to compare, in real-time, the first user profile to the first product identifier corresponding to the at least one ingredient of the first product obtained from the database;
   f) code to transmit, in real-time, to the at least one hand-held communication device, the results of the comparison of the first user profile to the first product identifier corresponding to the at least one ingredient of the first product, wherein the results are used to: (1) output an alert when the first product, based on the first user profile, includes a harmful ingredient; and (2) output an alert when the first product, based on the first user profile, includes a recommended ingredient;
   g) code to capture, in real-time, a second product identifier received by scanning a second product by the at least one hand-held communication device, wherein the second product includes indicia associated with the second product identifier;

h) code to transmit, in real-time, the second product identifier from the at least one hand-held communication device to the database;

i) code to compare, in real-time, the first user profile to the second product identifier corresponding to the at least one ingredients of the second product obtained from the database; and j) code to transmit, in real-time, to the at least one hand-held communication device, the results of the comparison of the first user profile to the second product identifier corresponding to the at least one ingredient of the second product, wherein the results are used to: (1) output an alert when the second product, based on the first user profile, includes a harmful ingredient; and (2) output an alert when the second product, based on the first user profile, includes a recommended ingredient.

2. The system of claim 1, wherein the user health information is selected from the group consisting of: allergies, prescriptions, chronic illness, medical condition, and dietary preferences.

3. The system of claim 1, wherein each of the users associated with the first user profile are in the same household.

4. The system of claim 1, wherein the results are further used to suggest a substitute ingredient.

5. The system of claim 1, wherein the results are further used to suggest a substitute product.

* * * * *